United States Patent [19]

Parravacini

[11] Patent Number: 4,878,909
[45] Date of Patent: Nov. 7, 1989

[54] HIGH EFFICIENCY CARDIAC VALVE

[76] Inventor: Roberto Parravicini, Viale Reiter, 51, 41100 Modena, Italy

[21] Appl. No.: 249,947

[22] Filed: Sep. 27, 1988

[30] Foreign Application Priority Data

Oct. 6, 1987 [IT] Italy ............................... 22167 A/87

[51] Int. Cl.⁴ ............................................... A61F 2/24
[52] U.S. Cl. ........................................ 623/2; 137/512; 137/527
[58] Field of Search .................... 623/2; 137/512, 527, 137/527.8

[56] References Cited

U.S. PATENT DOCUMENTS 4,178,638 12/1979 Meyer ...................................... 623/2
4,352,211 10/1982 Parravicini ............................. 623/2
4,357,715 11/1982 Klawitter ............................... 623/2
4,406,022 9/1983 Roy ........................................ 623/2

Primary Examiner—Ronald L. Frinks
Attorney, Agent, or Firm—Bucknam and Archer

[57] ABSTRACT

The cardiac valve comprises an annular body, at one end of which there are pivoted valve members, adapted to operate as a closing element, the annular body consisting of an outer ring member and an inner ring member which are mutually coupled, one of the ring members defining the pivot seats of the valve members, whereas the other ring member is adapted to delimit these seats, in order to provide a stable pivoting coupling of the valve members to the annular body.

3 Claims, 2 Drawing Sheets

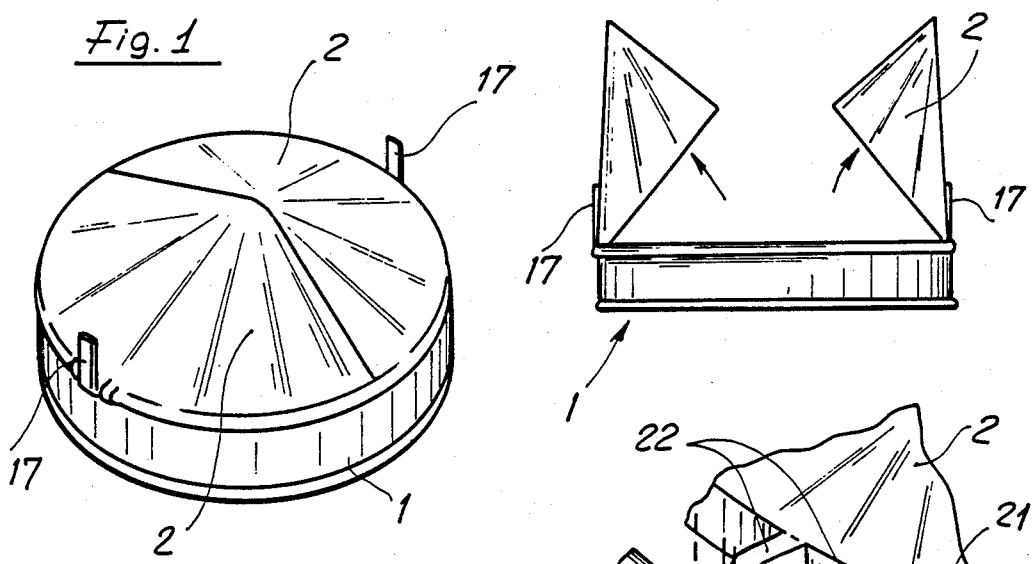
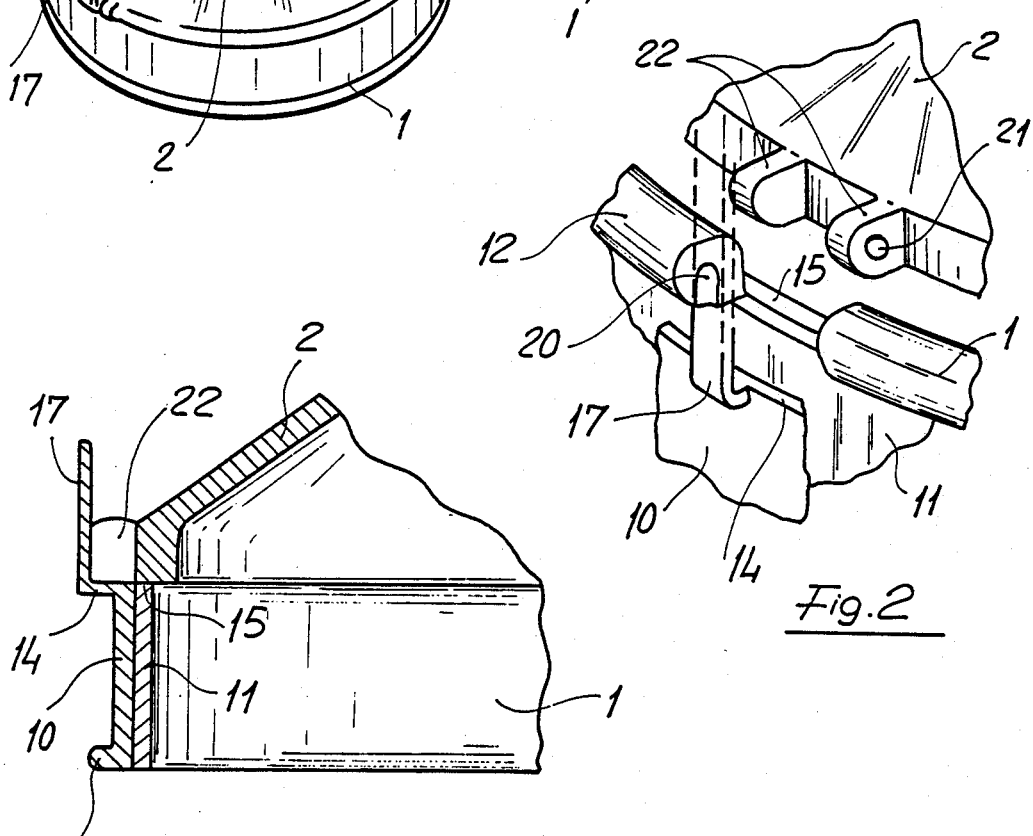
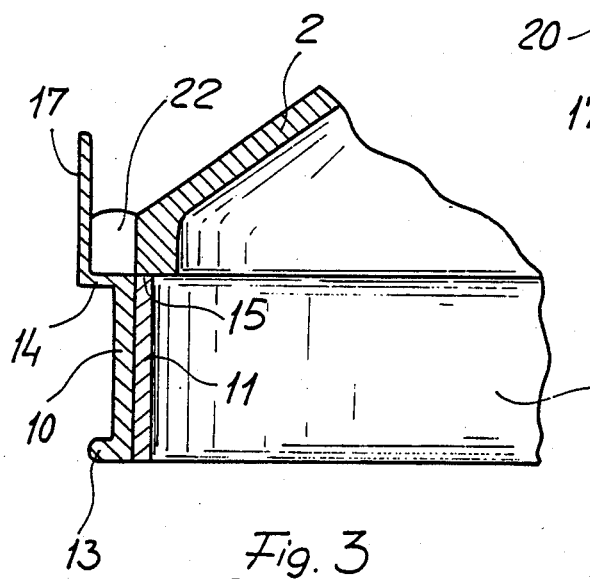

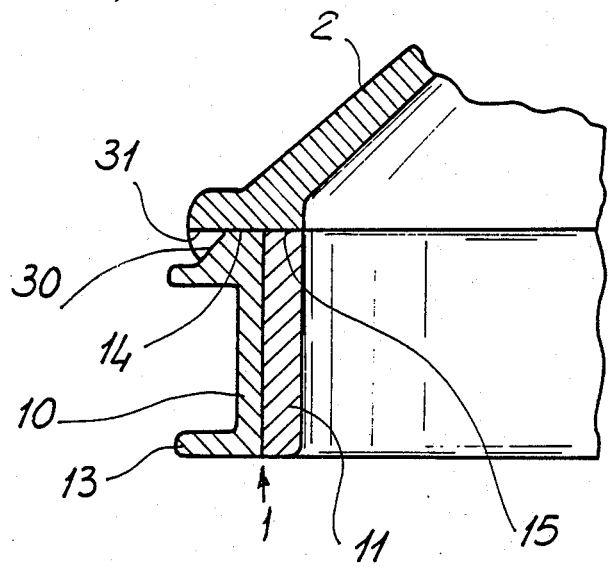
Fig. 6
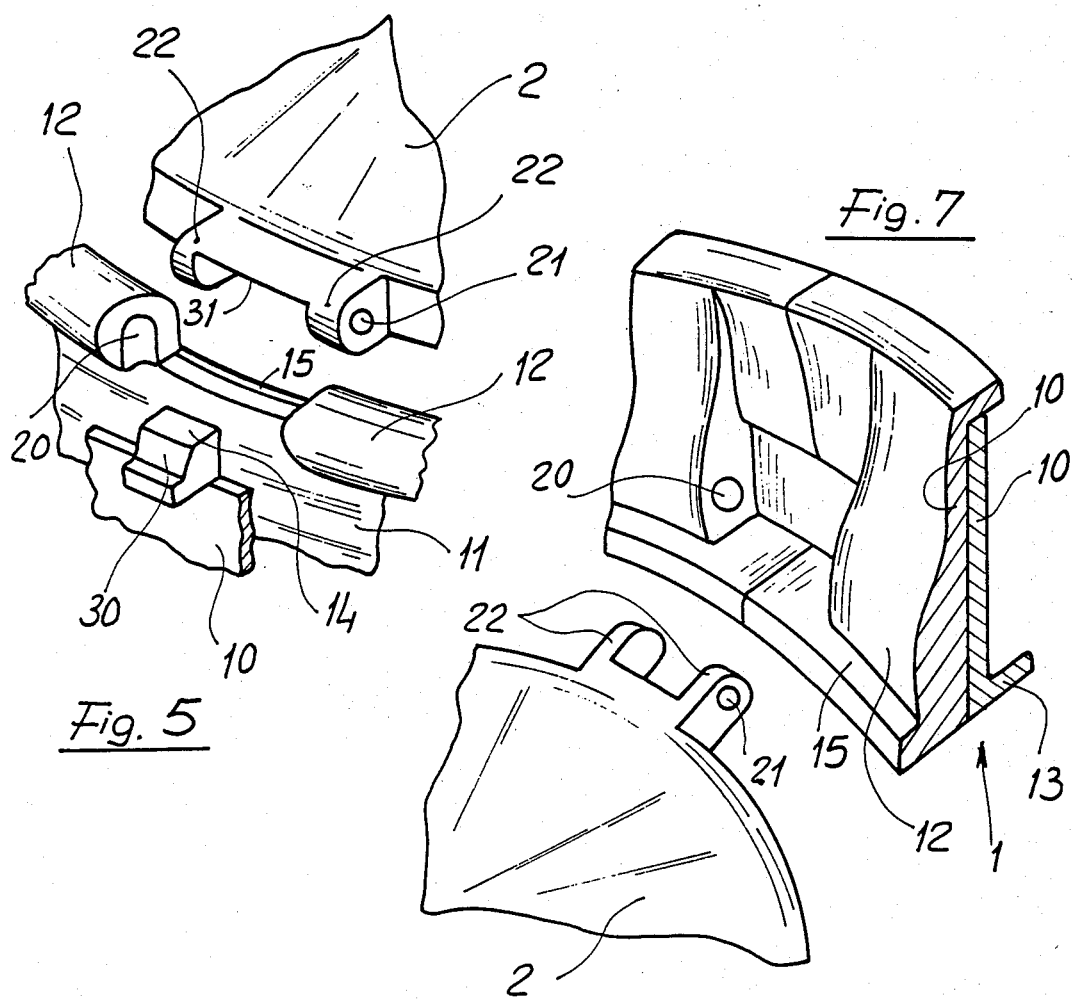
Fig. 7
Fig. 5

HIGH EFFICIENCY CARDIAC VALVE

BACKGROUND OF THE INVENTION

The present invention relates to a high efficiency cardiac valve structure, which substantially consists of an annular portion having, at one axial end thereof, a pair of valve members of substantial arc-shaped configurations, which valve members are hinged or pivoted to the annular body.

More specifically, said valve members are so arranged and designed as to provide a one-way valve able of opening as the blood flows in a direction, and of automatically closing as the blood flows in the opposite direction.

Cardiac valves are generally known which, even if they have been found to be satisfactory from the operational standpoint, are however susceptible to further improvements, mainly with respect to the coupling of the valve members to the ring element.

SUMMARY OF THE INVENTION

Thus, the task of the present invention is to overcome the above mentioned drawback, by providing a cardiac valve structure, which is very safe and efficient in operation, while providing a very efficient and stable coupling to the ring element associated therewith.

Within the scope of the above mentioned task, a main object of the present invention is to provide such a cardiac valve structure which can be simply, easily and quickly assembled.

Another object of the present invention is to provide such a cardiac valve structure which can be easily made starting from easily available elements and materials and which, moreover, is of a comparatively reduced cost.

According to one aspect of the present invention, the above mentioned task and objects, as well as yet other objects, which will become more apparent hereinafter, are achieved by a high efficiency cardiac valve comprising an annular body at one end of which there are hinged valve members adapted to operate as a closing element, characterized in that said annular body consists of an outer ring and an inner ring, coupled to one another, one of said rings defining the pivoting seats of said valve members, the other ring member being adapted to delimit said seats, in order to provide a stable pivoting coupling of said valve members to said annular body.

BRIEF DESCRIPTION OF THE DRAWINGS

Further caracteristics and advantages of the present invention will become more apparent hereinafter from the following description of three preferred, though not exclusive, embodiments of a cardiac valve structure which is illustrated, by way of an indicative example, in the accompanying drawings, where:

FIG. 1 is a schematic perspective view illustrating the cardiac valve structure according to the invention in its closing condition;

FIG. 2 is a perspective view illustrating a detail of the coupling of one of the valve members to the annular body;

FIG. 3 is a diametrical cross-sectional view illustrating the cardiac valve structure according to the invention;

FIG. 4 is an elevation side view illustrating the cardiac valve structure according to the invention;

FIG. 5 is a further perspective view illustrating the cardiac valve provided which different means for limiting the opening angular position of the valve members;

FIG. 6 is a diametrical cross-sectional view illustrating the subject cardiac valve structure having different means for limiting the opening angular positions of the valve members; and FIG. 7 is yet another perspective view illustrating the subject cardiac valve structure with its valve members hinged or pivoted, at the inlet of the cardiac valve, on the ring element formed in two pieces.

DESCRIPTION OF THE PREFERRED EMBODIMENTS

With reference to the figures of the accompanying drawings, the high efficiency cardiac valve structure according to the present invention comprises an annular body, indicated overally at the reference number 1, at one axial end of which there are hinged or pivoted two valve members 2.

A main feature of the invention is that the annular body 1 consists of an outer ring member 10 and an inner ring member 11 which are mutually coupled. More specifically, said inner ring member 11 is provided with a projecting rim 12 and a bearing surface 15, at an axial end thereof, whereas said outer ring member 10 defines a flanged rim 13 at the opposite axial end, and a closing surface 14.

The inner ring member 11 is made either as a single piece, or it is preferably made in two pieces.

On the projecting rim 12 there is provided a cut-out, therein there are formed seats 20 for pivoting the valve members 2, by coupling centering and guiding pin members 21, formed on the ears 22 projecting laterally from the valve member.

The above mentioned two valve members 2 have preferably a tapering shape and are able of mutually mating during the closure step, so as to close the opening defined by the bearing surface 15 of the inner ring member 11 of the annular body 1.

Preferably said seats 20 are of the opened type, as the inner ring member 11 is made of a single piece or, preferably of the closed type, as the inner ring member 11 consists of two pieces, which is a main feature of the invention, since this affords the possibility of easily and quickly assembling the cardiac valve.

In this connection it should be apparent that as the inner ring member is coupled to the outer ring member, which closes the seat 20, a very stable pivoting zone will be obtained, thereby assuring a reliable operation of the pivot coupling.

In order to limit the angular positions of the valve members 2 during the opening step, the outer ring member 11 is provided with lugs 17 which substantially extend along an axial direction and can be inserted through the ears 22 so as to provide an abutment function for the abutment of the valve members 2 as they are rotated to the opening positions.

According to a modified embodiment, which is illustrated in FIGS. 5 and 6, the rotation abutment is formed by providing a slanted abutment portion 30 which is defined on the outer ring member 10 and is adapted to abut against an abutment portion 31 defined by the valve members.

According to a further embodiment, which is shown in FIG. 7, the inner ring member 11 comprises the projecting rim 12 arranged at the inlet of the cardiac valve inside the ring member 11. In this case, the inner ring member 11 is split into two pieces and comprises closed seats 20.

The rotation abutment function is in this case provided by the inner surface of the inner ring member 11.

I claim:

1. A high efficiency artificial cardiac valve, comprising an annular body and valve members, said annular body consisting of an outer ring member and an inner ring member coupled to one another, said inner ring member, at one axial end thereof, defining a projecting rim therein there are formed pivot seat means of said valve members and a bearing surface, said outer ring member defining a flanged rim and a closure surface, said outer ring member and inner ring member being arranged with a concentrical and coaxial relationship with respect to one another, said pivot seat means being formed in a portion of said projecting rim of said inner ring member, said inner ring member being split into two pieces and said seat being closed.

2. An artificial cardiac valve according to claim 1, said valve members comprising ears with centering and guiding pins, and said cardiac valve further comprising a lug extending from said outer ring member and arranged between said ears.

3. An artificial cardiac valve according to claim 2, wherein said cardiac valve comprises an abutment slanted portion extending from said outer ring member and arranged between said ears.

* * * * *